United States Patent [19]

Van Valkenburg

[11] Patent Number: 5,038,794
[45] Date of Patent: * Aug. 13, 1991

[54] CAPILLARY BLOOD COLLECTOR AND METHOD

[76] Inventor: Nanci L. Van Valkenburg, 2149 Lark Ct. S., Wichita, Kans. 67209

[*] Notice: The portion of the term of this patent subsequent to Dec. 20, 2005 has been disclaimed.

[21] Appl. No.: 260,282

[22] Filed: Oct. 29, 1988

Related U.S. Application Data

[63] Continuation-in-part of Ser. No. 121,418, Nov. 16, 1987, Pat. No. 4,791,938.

[51] Int. Cl.⁵ .............................................. A61B 5/00
[52] U.S. Cl. .................................. 128/763; 604/317; 604/403
[58] Field of Search ................ 128/763, 767; 604/317, 604/403; 141/331, 343; 248/94; 222/460–462

[56] References Cited

U.S. PATENT DOCUMENTS

| | | |
|---|---|---|
| 3,902,477 | 9/1975 | Gerarde ............................. 604/403 |
| 4,024,857 | 5/1977 | Blecher et al. ....................... 128/763 |
| 4,132,225 | 1/1979 | Whattam ............................. 128/767 |
| 4,215,700 | 8/1980 | Crouther et al. ................... 128/763 |
| 4,411,163 | 10/1983 | White ................................... 128/763 |
| 4,646,753 | 3/1987 | Nugent ............................... 128/763 |
| 4,653,512 | 3/1987 | Losada ............................... 128/763 |

Primary Examiner—Max Hindenburg
Attorney, Agent, or Firm—John Wade Carpenter

[57] ABSTRACT

A capillary blood collector having a collection tube with a collar secured thereto. A bowl is provided with a capillary tube secured to the bowl bottom and communicating with an opening in the bottom of the bowl. A plurality of legs are attached to the bowl and extend downwardly therefrom. Each leg has at least one recess that is adaptable to removably receive the collar. A method for collecting blood comprising lodging the collar in the recess of each leg, depositing blood in the bowl to gravity feed through the capillary tube into the collection tube, and removing the collar from within the recess and lodging the open top of the collection tube against the bottom of the bowl.

19 Claims, 4 Drawing Sheets

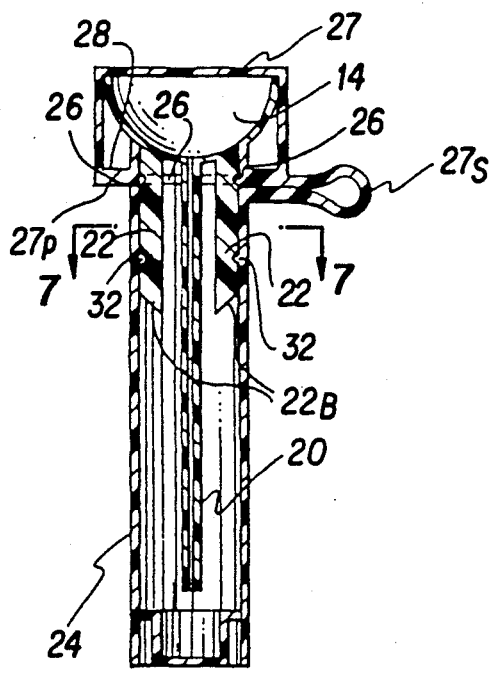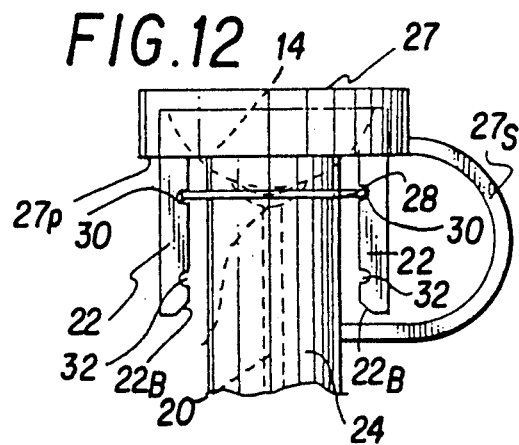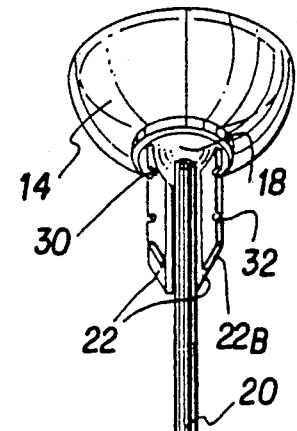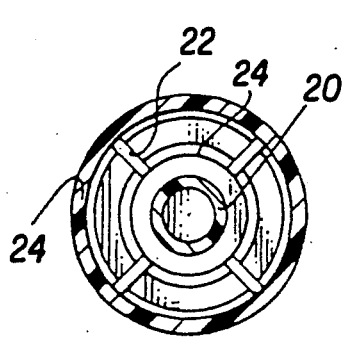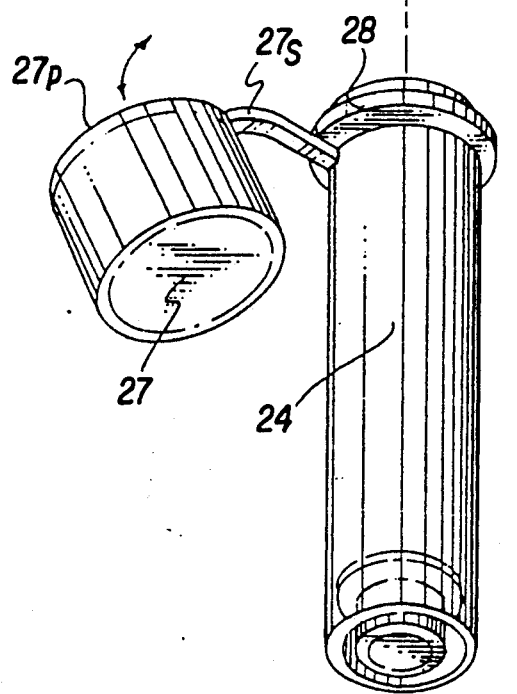

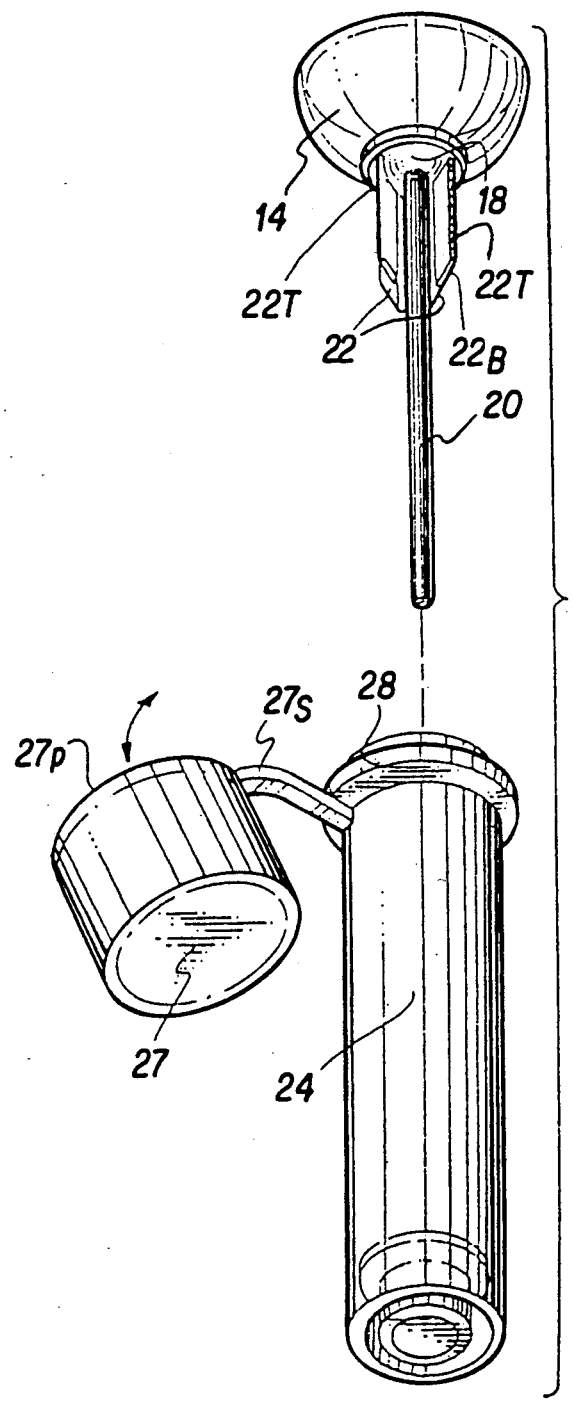
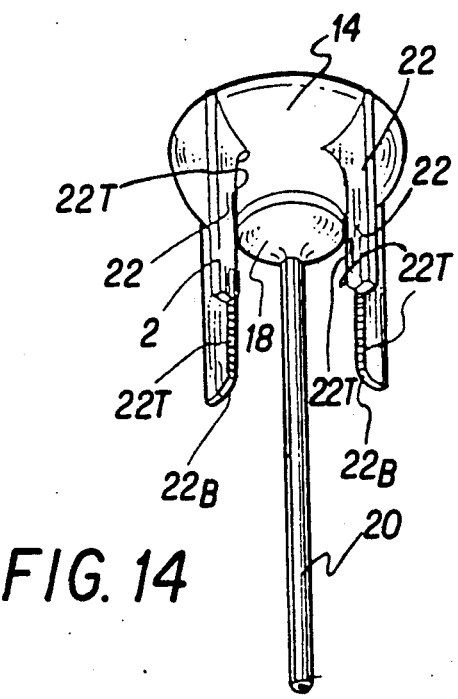
FIG. 13
FIG. 14

CAPILLARY BLOOD COLLECTOR AND METHOD

This is a continuation-in-part application of copending application having Ser. No. 121,418, filed Nov. 16, 1987, now U.S. Pat. No. 4,791,938.

FIELD OF THE INVENTION

This invention is related to a capillary blood collector. More specifically, this invention provides a capillary blood collector to safely collect blood within a collection tube, and a method for collecting blood.

DESCRIPTION OF THE PRIOR ART

The following United States patents by numbers were discovered in a patentability investigation: U.S. Pat. Nos. 4,646,753; 4,653,512; 4,411,163; 4,132,225; 4,215,700; and 4,024,857. None of the foregoing patents teach or suggest the particular capillary blood collector and method of this invention.

SUMMARY OF THE INVENTION

The present invention broadly accomplishes its desired objects by providing for a capillary blood collector comprising a collection tube having a tube top. An inner collar is circumferentially disposed around the inside of the collection tube in proximity to the tube top. The capillary blood collector additionally comprises a bowl having a bowl bottom with a bowl opening; and a capillary tube secured to the bowl bottom and communicating with the bowl opening. At least one leg is supported by the bowl in a depending relationship. The leg has an inner leg face and an outer leg face. The leg also has a structure defining a lower recess and an uppr recess on the outer leg face. The leg removably connects to the inner collar of the collection tube such that the capillary tube extends into the collection tube and the bowl is supported in an elevated relationship above the collection tube.

The present invention further accomplishes its desired objects by broadly providing a capillary blood collector comprising a collection tube having a tube top. An outer collar is circumferentially disposed around the outside of the collection tube in proximity to the tube top. The capillary blood collector additionally comprises a bowl having a bowl bottom with a bowl opening; and a capillary tube secured to the bowl bottom and communicating with the bowl opening. At least one leg is supported by the bowl in a depending relationship. The leg has an inner leg face and an outer leg face, and a structure defining a lower recess and an upper recess on the inner leg face. The leg removably connects to the outer collar such that the capillary tube extends into the collection tube and is supported in an elevated relationship above the collection tube.

The present invention still further accomplished its desired objects by broadly providing a method for collecting blood comprising the steps of:

a) providing a collection tube having a collar secured thereto;

b) providing a bowl having a bowl bottom with a bowl opening and a capillary tube secured to the bowl bottom and communicating with the bowl opening, and at least one leg supported by the bowl in a depending relationship and the leg having a lower recess and an upper recess;

c) inserting the capillary tube into the collection tube;

d) positioning the collar in the lower recess of the leg;

e) depositing blood into the bowl such that the blood flows through the bowl opening and through the capillary tube and into the collection tube; and f) removing the collar from the lower recess and positioning the collar into the upper recess of the leg.

It is therefore an object of the invention to provide for a capillary blood collector.

It is another object of the invention to provide for a method for collecting blood.

These, together with the various ancillary objects and features which become apparent to those skilled in the are as the following description proceeds, are attained by this novel capillary blood collector and process, a preferred embodiment being shown with reference to the accompanying drawings, by way of example only, wherein:

BRIEF DESCRIPTION OF THE DRAWINGS

FIG. 5 is a vertical sectional view in direction of the arrows and along the plane of line 5—5 in FIG. 2;

FIG. 6 is an exploded segmented perspective view of the embodiment of the capillary blood in FIGS. 1, 2 and 5;

FIG. 7 is a horizontal sectional view taken in direction of the arrows and along the plane of line 7—7 in FIG. 5;

FIG. 12 is a partial vertical side elevational view of the bowl-capillary tube combination having the upper recesses of the legs engaged to an outer collar mounted around the top of the collection tube with a cap flexible engaged to the collection tube and removably engaged to and over the top of bowl and upper part of the legs;

FIG. 13 is an exploded segmented perspective view of the embodiment of the blood collector having threaded legs; and FIG. 14 is a perspective of another embodiment of the blood collector wherein threaded legs are secured to the bowl.

DETAILED DESCRIPTION OF THE INVENTION

Figure 1:
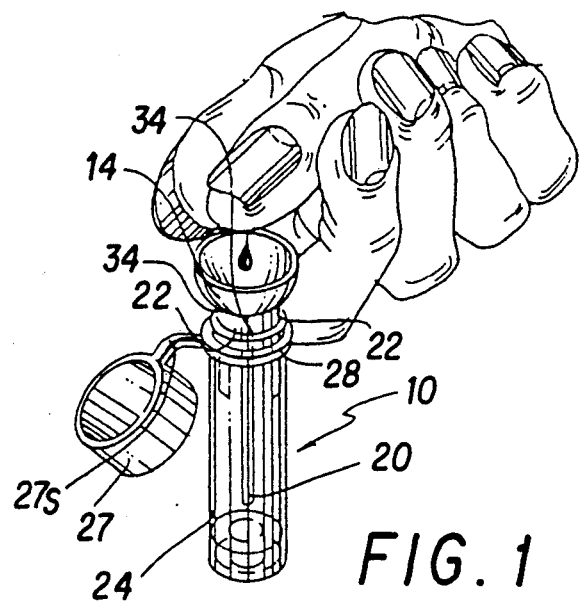
FIG. 1 is a perspective view of one embodiment of the capillary blood collector with the inner collar lodging in the lower recess of the legs lodging such that the bowl is in an elevated position to provide for an air space which allows the blood being desposited to flow by gravity through the capillary tube and into the collection tube.
Figure 2:
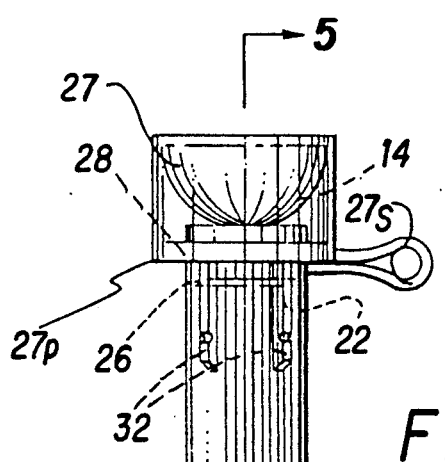
FIG. 2 is a side elevational view of the embodiment of the capillary blood collector in FIG. 1 with the inner collar lodging in the upper recess of the legs such that the bottom of the bowl firmly seals the top of the collection tube and with the cap positioned over the top of the bowl.
Figure 3:
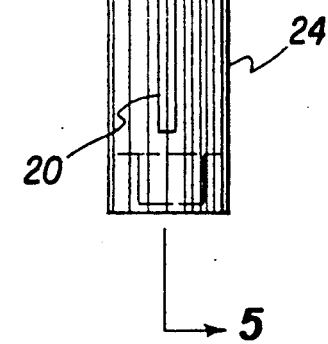
FIG. 3 is a top plan view of the bowl.
Figure 4:
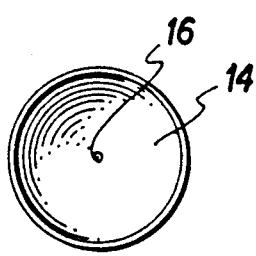
FIG. 4 is a bottom plan view of the collection tube without the cap secured thereto.

Referring in detail now to the drawings wherein similar parts of the invention are identified by like reference numerals, there is seen a capillary blood collector, generally illustrated as 10, with two preferred embodiments respectively illustrated in FIGS. 1-7 and 8-12. Both preferred embodiments comprise a bowl means 14 with a bowl opening 16 at the bottom of the bowl 14. The "bowl means 14" as to be interpreted herein including the claims may be defined as any suitable hemispherical bowl means or partial hemispherical bowl means (e.g. a spoon-shaped means) that is capable of performing the function of receiving blood and causing the blood to flow into a tubular, hollow capillary member 20. The bowl 14 preferably (but not necessarily as shown in FIG. 5) is formed with a plate member 18 that has a plate opening (not shown in the drawings) that registers with the bowl opening 16. The tubular, hollow capillary member 20 connects to the bowl opening 16 such that the hollow capillary member 20 communicates with the bowl opening 16. Alternatively, as illustrated in FIG. 5, the hollow capillary member 20 connects directly to the bottom of the bowl 14 and around the bowl opening 16 such that the inside of the tubular hollow capillary member 20 communicates with the bowl opening 16. Both preferred embodiments of the invention also comprise at least one leg means 22, preferably a plurality of legs 22, and a collection tube or vial 24.

In the preferred embodiment for the capillary blood collector 10 in FIGS. 1-7, the legs 22 may either be connected to the plate member 18 (see FIG. 6) or to the outside bottom of the bowl 14 (See FIG. 5) when no plate member 18 has been used. For this embodiment of the invention, an inner collar 26 is disposed around the inside of the collection tube 24. Inner collar 26 protrudes away from the inside cylindrical wall of the collection tube 24. A cap 27 is formed with a perimeter 27p and with a flexible strap 27s which secures to the top of the side of the collection tube 24. An outer collar 28 may or may not be employed. If an outer collar 28 is used in the embodiment of the invention in FIGS. 1-7, the strap 27s secures to the side of the collection tube 24 underneath the outer collar 28 such that the structural perimeter 27p of the cap 27 can fit snugly around the outer collar 28. Each of the legs 22 has at least one recess, preferably an upper recess 30 and a lower recess 32 on the outer face of the leg 22. The lower recess 32 and the upper recess 30 are for both removably receiving the protruding inner collar 26 therein. As illustrated in FIG. 13, the recesses 30 and 32 may be part of a plurality of threads 22T on the outer face of the leg 22. Thus, whenever "recess" is stated herein for this embodiment including the claims, it is to be construed to mean a single thread which is part of the plurality of threads 22T on the outer face of the leg 22.

In operation of the preferred embodiment for the capillary blood collector 10 in FIGS. 1-7, the legs 22 (along with the depending, hollow capillary tube 20) are inserted into the collection tube 24 until the inner collar 26 snaps into the lower recess 32 of each leg 22. Such a fitting supports the bowl 14 in an elevated position above the top opening of the collection tube 24 with a vent (or air opening) 34 between the outside bottom of the bowl 14 and the top opening of the collection tube 24 (See FIG. 1). When blood or any other fluid is deposited into the bowl 14, the vent opening 34 allows the blood (or other fluid) to flow through the bowl opening 16, through the hollow capillary tube 20 and into the bottom of the collection tube 24. After the desired quantity of blood (or other fluid) has been collected, the inner collar 26 is removed from within the lower recess 32 of each leg 32, such as by merely pushing down with force on top of the elevated bowl 14. The legs 22 are preferably manufactured of flexible material (e.g. polyethylene) in order to bend towards the axis of the capillary tube 20 when force is applied on top of the bowl 14. When the legs 22 bend accordingly, the inner collar 26 pops out of the lower recess 32 of each leg 22, allowing the freedom to insert the legs 22 (along with the depending, hollow capillary tube 20) further into the collection tube 24. Preferably, the legs 22 (and the depending capillary tube 20) are pushed all the way into the collection tube 24 until the inner collar 26 snaps into the upper recess 30 of each leg 22. To facilitate the passing of the bottom of each leg 22 over the inner collar 26 and the inward bending of each leg 22, each leg 22 has a beveled bottom 22b.

In operation of the preferred embodiment for the capillary blood collector 10 in FIGS. 1-7 except with the legs 22 containing a plurality of threads 22T on the outer face thereof as illustrated in FIG. 13, the threaded legs 22 (along with the depending, hollow capillary tube 20) are inserted into the collection tube 24. The legs 22 are disposed to threadably engage the inner collar 26 by rotating the legs 22 (which necessarily includes the attached bowl means 14 being rotated) against the inner collar 26. Such threadable engagement of the threaded legs 22 with the inner collar 26 is to the degree that only the lower part of the threaded legs 22 threadably engage the inner collar 26. Such a fitting supports the bowl 14 in an elevated position above the top opening of the collection tube 24 with the vent (or air opening) 34 being situated between the outside bottom of the bowl 14 and the top opening of the collection tube 24. After the desired quantity of blood has been collected, the threaded legs 22 (including the attached bowl 14) are further rotated in a fashion as a bolt threadably passing into and through a threaded nut. As the threaded legs 22 are being further rotated against the inner collar 26, the legs 22 including the attached bowl 14 travel downwardly. The threaded legs 22 and the attached bowl 14 are continually rotated until the outside bottom of the bowl 14 snugly fits or seats around the top opening of the collection tube 24 in order to seal-off or shut-in the open top of the collection tube 24. To further seal-off the top of the bowl 14, cap 27 is snapped over the structural perimeter of the top opening of the bowl 14 (see FIGS. 2 and 5).

In a preferred embodiment of the invention, when the inner collar 26 is disposed within the upper recess 30 of each leg 22 (or threaded against/around the uppermost threads of the plurality of threads 22T), the outside bottom of the bowl 14 snugly fits or seats around the top opening of the collection tube 24 (see FIG. 5) to firmly seal-off or shut-in the open top of the collection tube 24, thus preventing any of the enclosed fluid from flowing out. To further seal-off or shut-in the open top of the collection tube 24, the cap 27 is positioned over the open top of the bowl 14 and the perimeter 27p of the cap 27 is snapped over the perimeter of the outer collar 28 to fit snugly thereagainst (see FIG. 5). The cap 27 affords another means for enclosing and maintaining the fluid within the collection tube 24, thus preventing the remote possibility of fluid being spilled from the collection tube 24 by flowing out of the collection tube 24 through the hollow capillary tube 20 and the bowl opening 16. When it is desired to remove the fluid from the collection tube 24, the cap 27 is merely snapped off the perimeter of the outer collar 26, and the bowl 14 is grasped and pulled up forcefully to flex or bend the flexible legs 22 inwardly to disenlodge the inner collar 26 from within the upper recess 30 of each leg 22, and from within the lower recess 32 of each leg 22 in the event the inner collar 26 comes to rest within the lower recess 32 of each leg 22 as the bowl 14 (along with the depending legs 22 and capillary tube 20) are being pulled upwardly.

Figure 8:
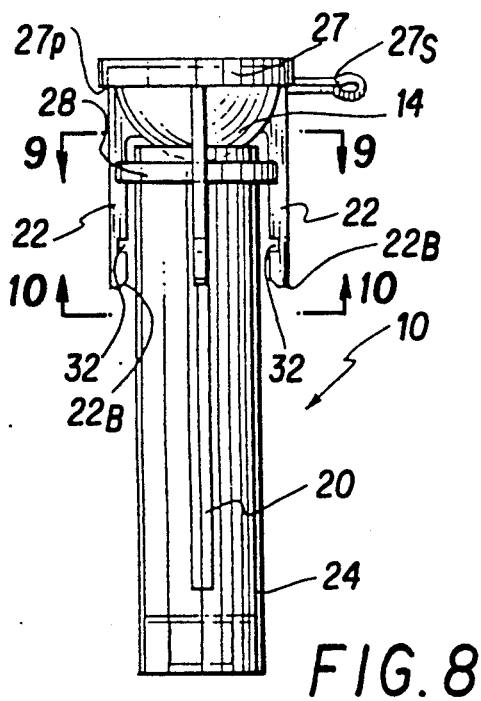
FIG. 8 is a side elevational view of another embodiment of the capillary blood collector.
Figure 9:
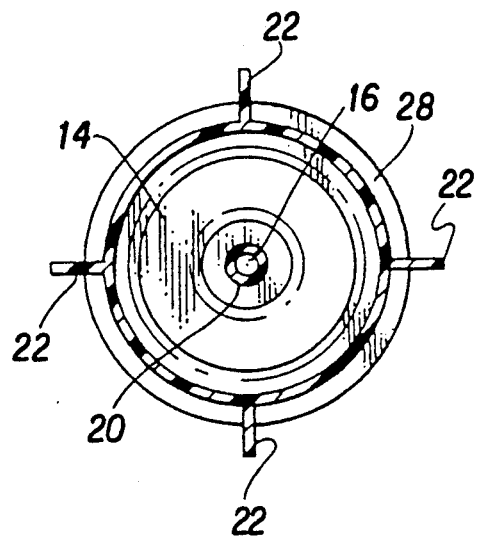
FIG. 9 is a horizontal sectional view taken in direction of the arrows and along the plane of line 9—9 in FIG. 8.
Figure 10:
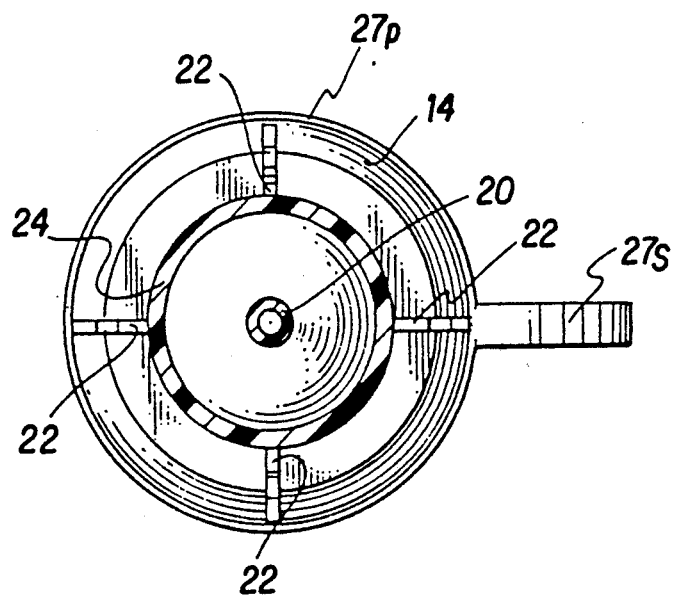
FIG. 10 is a horizontal section view taken in direction of the arrows and along the plane of line 10—10 in FIG. 8.
Figure 11:
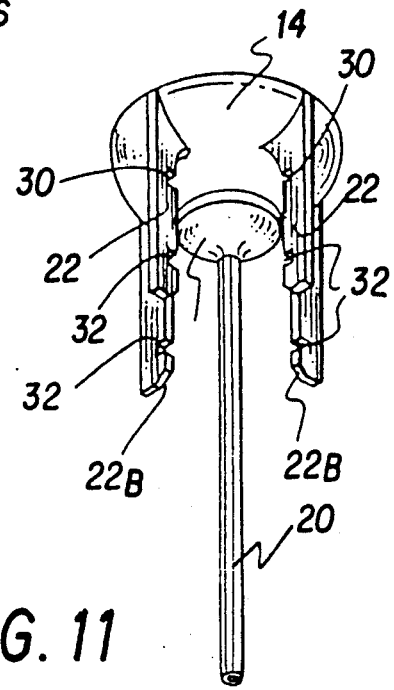
FIG. 11 is a perspective view of the bowl-capillary tube combination having the legs with recesses on the inside faces and connected to the bowl.

In the preferred embodiment for the capillary blood collector 10 in FIGS. 8-12, the legs 22 are secured to the outside bottom of the bowl 14 such that the outside face of each leg 22 collimates with the structural perimeter that circumscribes the top opening of the bowl 14 (as illustrated in FIGS. 8, 11 and 12). The lower recess 32 and the upper recess 30 are formed on the inner face of each leg 22. The outer collar 28 is secured to the outside of the collection tube 24 in proximity to the top thereof and protrudes therefrom. The recesses 30 and 32 are for removably receiving the protruding outer collar 28 therein. The plate member 18 may or may not be employed (see FIGS. 8 and 10 where plate member 18 is not used and see FIG. 11 where plate member 18 is used). The flexible strap 27s of the cap 27 is either secured to the outside of the bowl 14 (see FIGS. 8 and 10) or is secured to the outside of the collection tube 24 (see FIG. 12) and underneath the outer collar 28. The inner collar 26 may or may not be employed. As illustrated in FIG. 14, the recesses 30 and 32 may be part of a plurality of threads 22T on the inner face of the leg 22. Thus, whenever "recess" is stated herein for this embodiment including the claims, it is to be construed to mean a single thread which is part of the plurality of threads 22T on the inner face of the leg 22.

The operation of the preferred embodiment for the capillary blood collector 10 in FIGS. 8-12 is similar to that of FIGS. 1-7. More specifically, the depending capillary tube 20 is inserted into the inside of the collection tube 24 with legs 22 passing over the outside of the collection tube 24 and over the outer collar 28. The legs 22 are flexible such as to bend slightly away from the axis of the capillary tube 20, enabling the legs 22 to flex outwardly and allowing the outer collar 28 to snap into the lower recess 32 of each leg 22 which would enable the bowl 14 to be supported in an elevated position above the top opening of the collection tube 24 with the vent 34 between the outside bottom of the bowl 14 and the top opening of the collection tube 24. To facilitate the passing of the bottom of each leg 22 over the outer collar 28 and the outward bending of each leg 22, each leg 22 has a beveled bottom 22b. After the desired quantity of fluid has been collected the outer collar 28 is removed from within the lower recess 32 of each flexible leg 22 such as by merely pushing down with force on top of the elevated bowl 14. When the legs 22 bend outwardly, the outer collar 28 pops out of the lower recess 32 of each flexible leg 22, permitting the capillary tube 20 to be inserted further into the collection tube 24 and allowing the legs 22 to be slid further down the outside of the outer collar 28 until the outer collar 28 snaps into the upper recess 30 of each flexible leg 22. In such a posture, the outside bottom of the bowl 14 snugly fits or seats around the top opening of the collection tube 24 (see FIGS. 8 and 12) to firmly seal-off or shut-in the open top of the collection tube 24. This prevents any of fluid contained within the collection tube 24 from flowing out. To seal-off the top of the bowl 14, the cap 27 is positioned over the open top of the bowl 14 and the perimeter 27p of the cap 27 is snapped over the structural perimeter of the top opening of the bowl 14 and over the top portion of the outer face of each leg 22 (see FIGS. 8 and 12). The cap 27 in such an enclosing position prevents the fluid within the collection tube 24, from leaving the collection tube 24 through the hollow capillary tube 24 and the bowl opening 16. When it is desired to remove the fluid from the collection tube 24, the cap 27 is snapped off the structural perimeter of the top opening of the bowl 14 and off the top portion of the outer face of each leg 22, and the bowl 14 is firmly grasped and pulled upwardly with force to flex the legs 22 inwardly and to disenlodge the outer collar 28 from within the upper recess 30 of each leg 22 continual forceful pulling upwardly of the bowl 14 would also disenlodge the outer collar 28 from within the lower recess 32 of each leg 22 as the bowl 14 along with the depending capillary tube 20 are being pulled upwardly.

The operation of the preferred embodiment for the capillary blood collector 10 in FIGS. 8-12, except with the legs 22 containing a plurality of threads 22T on the inner face thereof as illustrated in FIG. 14, is similar to the embodiment in FIGS. 1-7 except with the legs 22 having the threads 22T on the outer face thereof as illustrated in FIG. 13. More specifically, the depending capillary tube 20 is inserted into the inside of the collection tube 24 with threaded legs 22 passing over the outside of the collection tube 24. The lowermost part of the threaded legs 22 contacts the outer collar 28. The threaded legs 22 (including the attached bowl 14) are rotated such that the lowermost part of the threaded legs 22 begin to threadably engage the outer collar 28. Such threadable engagement is terminated when the desired vent (or air opening) 34 is between the outside of the bottom of the bowl 14 and the top opening of the collection tube 24. After the desired quantity of fluid or blood has been collected, the threaded legs (including the attached bowl 14) are continually rotated about the outer collar 28 such that the threaded legs 22 and the attached bowl 14 travel downwardly towards the collection tube 24. Rotation is continued until the outside bottom of the bowl 14 snugly fits or seats around the top opening of the collection tube 24 (similar to the posture in FIGS. 8 and 12) to firmly seal-off or shut-in the open top of the collection tube 24. As was previously indicated, this prevents any of the fluid or blood contained in the collection tube 24 from flowing out. For this embodiment of the invention, in order to further seal-off the top of the bowl 14, the cap 27 (see FIG. 8) is positioned over the top of the bowl 14 and the perimeter 27p of the cap 27 is snapped over the structural perimeter of the top opening of the bowl 14 and over the top portion of the outer face of each threaded leg 22.

While the present invention has been described herein with reference to particular embodiments thereof, a latitude of modification, various changes and substitutions are intended in the foregoind disclosure, and it will be appreciated that in some instances some features of the invention will be employed without a corresponding use of other features without departing from the scope of the invention as set forth.

By way of example only, the inner collar 26 and outer collar 28 may have their respective outermost perimetrical edges beveled, tapered, or otherwise narrowed, in order to facilitate the threadable engagement with threads 22T on the inner face or outer face of the treaded legs 22.

I claim:

1. A capillary blood collector comprising a collection tube having a tube top; an inner collar circumferentially disposed around the inside of said collection tube in proximity to said tube top;
   a bowl having a bowl bottom with a bowl opening;
   a capillary tube secured to said bowl bottom and communicating with said bowl opening;
   at least one leg supported by said bowl in a depending relationship, said leg having an inner leg face and an outer leg face, said leg having a structure defining at least one recess on said outer leg face; and said leg removably connects to said inner collar such that said capillary tube extends into said collection tube.

2. The capillary blood collector of claim 1 wherein said leg has a structure defining a plurality of threads on said outer leg face for removably recovering said inner collar.

3. The capillary blood collector of claim 1 wherein said at least one recess removably receives said inner collar.

4. The capillary blood collector of claim 2 wherein said plurality of threads threadably engage said inner collar for removably receiving the same.

5. The capillary blood collector of claim 2 additionally comprising a cap including a flexible strap bound to said collection tube such that said cap can be removably secured to said tube top and enclose said bowl.

6. The capillary blood collector of claim 2 additionally comprising a cap including a flexible strap bound to said bowl such that said cap can be removably secured over said bowl.

7. A capillary blood collector comprising a collection tube having a tube top; an outer collar circumferentially disposed around the outside of said collection tube in proximity to said tube top;
   a bowl having a bowl bottom with a bowl opening;
   a capillary tube secured to said bowl bottom and communicating with said bowl opening;
   at least one leg supported by said bowl in a depending relationship, said leg having an inner leg face and an outer leg face, said leg having a structure defining at least one recess on said inner leg face, and said leg removably connects to the outer collar such that the capillary tube extends into the collection tube.

8. The capillary blood collector of claim 7 wherein said leg has a structure defining a plurality of threads on said inner leg face for removably receiving said outer collar.

9. The capillary blood collector of claim 7 wherein said at least one recess removably receives said outer collar.

10. The capillary blood collector of claim 8 wherein said plurality of threads threadably engage said outer collar for removably receiving the same.

11. A method for collecting blood comprising the steps of:
    a) providing a collection tube having a collar secured thereto and an open tube top;
    b) providing a bowl having a bowl bottom with a bowl opening and a capillary tube secured to said bowl bottom and communicating with said bowl opening, and at least one leg supported by said bowl in a depending relationship and said leg having at least one recess;
    c) inserting said capillary tube into said collection tube;
    d) positioning said collar in said at least one recess of said leg;
    e) depositing blood into said bowl such that the blood flows through the bowl opening and through the capillary tube and into the collection tube; and
    f) removing said collar from said at least one recess and positioning said bowl bottom against said open tube.

12. The method of claim 11 wherein said leg comprises a plurality of threads containing said at least one recess.

13. The method of claim 12 wherein said removing step (f) comprises threadably rotating said leg around said collar.

14. A collection device for a capillary blood collector comprising a bowl having a bowl bottom with a bowl opening; a capillary tube secured to said bowl bottom and communicating with said bowl opening; at least one leg supported by said bowl in a depending relationship, said leg having an inner leg face and an outer leg face, said leg having a structure defining at least one thread defining at least one recess.

15. The device of claim 14 wherein said leg comprises a plurality of threads.

16. The device of claim 15 wherein said plurality of threads is disposed on the outer leg face.

17. The device of claim 15 wherein said plurality of threads is disposed on the inner leg face.

18. The device of claim 14 wherein said structure of said leg defines a lower recess and an upper recess on said outer leg face.

19. The device of claim 14 wherein said structure of said leg defines a lower recess and an upper recess on said inner leg face.

* * * * *